Figure 1:
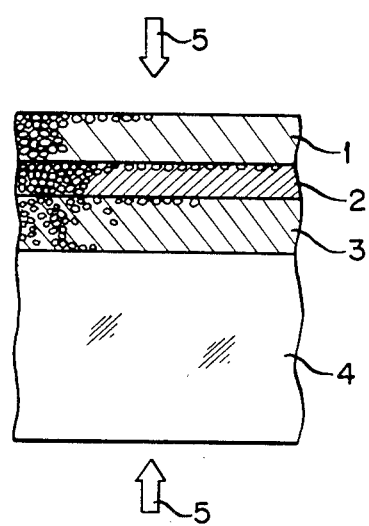

United States Patent [19]

Yasoshima et al.

[11] Patent Number: 4,613,567

[45] Date of Patent: Sep. 23, 1986

[54] IMMUNOASSAY METHOD FOR MEASURING IMMUNOLOGICAL ANTIGEN IN FLUID SAMPLE

[75] Inventors: Seikichi Yasoshima; Mikio Koyama; Kenichiro Okaniwa, all of Hino, Japan

[73] Assignee: Konishiroku Photo Industry Co., Ltd., Tokyo, Japan

[21] Appl. No.: 520,072

[22] Filed: Aug. 3, 1983

[30] Foreign Application Priority Data

Aug. 19, 1982 [JP] Japan ................................ 57-144341

[51] Int. Cl.⁴ ...................... C12Q 1/00; G01N 21/64; G01N 33/558; G01N 33/543
[52] U.S. Cl. ......................................... 435/7; 422/56; 422/57; 422/58; 436/514; 436/515; 436/535; 436/807; 435/805
[58] Field of Search ................ 435/7, 805; 422/56–58; 436/810, 807, 514, 515, 535

[56] References Cited

U.S. PATENT DOCUMENTS

| | | | |
|---|---|---|---|
| Re. 30,267 | 5/1980 | Bruschi | 422/58 |
| 4,255,384 | 3/1981 | Kitajima et al. | 422/58 |
| 4,294,817 | 10/1981 | Burgett et al. | 422/57 |
| 4,363,874 | 12/1982 | Greenquist | 422/56 |
| 4,390,343 | 6/1983 | Walter | 422/56 |
| 4,459,358 | 7/1984 | Berke | 422/56 |
| 4,472,498 | 9/1984 | Masuda et al. | 422/56 |

*Primary Examiner*—Christine M. Nucker
*Attorney, Agent, or Firm*—Frishauf, Holtz, Goodman & Woodward

[57] ABSTRACT

There is disclosed an immunoassay comprising carrying out an immunological reaction by contacting a fluid sample with an element for immunoassay, having at least three layers of a first detecting layer, a blocking layer and a second detecting layer which are successively laminated, the element containing a substance capable of binding specifically to an immunologically active substance in a fluid sample only in either one of the first and the second detecting layers, and then measuring the detected quantities corresponding to the immunological reaction quantities from both of the first and the second detecting layers.

The immunoassay by the use of the immunological analytical element according to this invention improves the precision immunoassay by measuring both of Bound and Free.

18 Claims, 1 Drawing Figure

IMMUNOASSAY METHOD FOR MEASURING IMMUNOLOGICAL ANTIGEN IN FLUID SAMPLE

This invention relates to an assay of a component present in a trace amount in a fluid sample, more particularly a quantitative immunoassay by the use of an analytical element.

As a method for quantifying a substance existing only in a trace amount in a fluid (especially a biological fluid sample), there have been employed various immunological reactions. An immunological reaction is a specific binding reaction between an immunologically active substance (e.g. antigen) in a fluid sample and a substance which binds specifically with said active substance (e.g. antibody), and various developments of analytical reactions have been done by utilizing this principle.

Particularly, in 1958, Berson and Yallow successfully measured insulin in serum by the use of insulin labeled with radioactive iodine $^{131}I$ and an antibody against insulin isolated from a diabetic patient.

Said radioimmunoassay (abbreviated as RIA) is a good quantitative analytical method having high sensitivity. However, since a radioisotope is used as the labeling compound, there are involved various drawbacks, such that special facilities are required and it is difficult to perform radioimmunoassay in ordinary laboratories, that greatest care is also required to be paid with respect to waste liquid and also that a radioisotope with short half-life period cannot be stored for a long time. For these reasons, methods in which such a radioisotope is replaced with other tags became of interest. Examples of such tag substances include enzymes, bacteriophages, metals and complexes of organometals, co-enzymes, enzyme substrates, enzyme inhibitors, cycle reactants, organic prosthetic groups, chemical luminescent reactants and fluorescent molecules, etc. Among them, presently used in practice for assay are the enzymeimmunoassay (EIA) using an enzyme and fluorescent immunoassay (FIA) using fluorescent molecules.

However, the above immunoassays conventionally used involve various drawbacks as mentioned below.

(1) As compared with conventional chemical analysis or blood analysis using a fluid sample typically of 10 to 200 μl, a relatively large quantity (e.g. 0.1 to 1.0 ml) of a fluid sample is necessary.

(2) It will take a long time (e.g. several hours to overnight) for the specific binding reaction of the test mixture.

(3) After completion of the reaction, physical separation of antigen-antibody bound conjugate from unbound materials (called B/F separation) is necessary.

(4) For completion of an immunological reaction, many steps are necessary, and those steps must be conducted individually and separately [e.g. the steps of sample addition, incubation, separation and quantifying of label (labeled compound)].

(5) Adaptation for automatic system is difficult.

On the other hand, an analytical system employing dry chemistry capable of overcoming these drawbacks is also disclosed in Japanese Provisional Patent Publication No. 90859/1980. This method comprises (i) applying a quantity of a sample comprising a mixture of an unlabeled antigen (fluid sample) with a quantity of fluorescence-labeled antigen on an element for immunoassay, said element typically having a structural layer (called as registration layer) comprising polymeric beads and a structural layer comprising colored polymeric beads containing an antibody immobilized therein successively coated on a flexible plastic support, thereby (ii) permitting the unlabeled antigen and the labeled antigen to bind competitively, and (iii) quantifying the antigen in the fluid sample by measuring the amount of the unaltered labeled antigen which migrates into the registration layer.

However, according to this method, the quantity of the unlabeled antigen in the fluid sample is determined by (A) detection of the unbound labeled antigen which migrates into the registration layer (called F detection) or by (B) detection of the bound labeled antigen bound to the immobilized antibody (called B detection). Such a method involves the drawback that there is a possibility to involve necessarily a great error, because the quantity of unlabeled antigen is determined by detection of either one of F and B. This is particularly remarkable in detecting a component existing only in a very minute amount. That is, the detection results of a component present in very small amount disadvantageously involve errors caused by formation and mixing of non-specific binding, scattering of coated film thicknesses, fluctuations in measuring conditions (e.g. luminance of light source, etc.), whereby reliability of the quantified values is lowered.

An object of this invention is to provide an immunoassay by the use of an analytical element having none of such various drawbacks as described above.

The present inventors have successfully overcome the above drawbacks by an immunoassay for measuring an immunologically active substance in a fluid sample, which comprises;

(1) bringing said fluid sample into contact with an immunological analytical element, wherein said element comprises a first detecting layer, a blocking layer and a second detecting layer which are successively laminated, and contains a substance capable of binding specifically to said immunologically active substance in either one of said first and second detecting layers;

(2) carrying out an immunological reaction so as to produce an immunological reaction quantity; and (3) measuring a detected quantity corresponding to said immunological reaction quantity from both of said first and second detecting layers.

FIG. 1 shows a sectional view of one embodiment of the analytical element according to this invention.

This invention is to be described in detail below.

This invention relates to an immunoassay, which comprises, for example, assaying at the same time a conjugate in which a labeled antigen is bound to an antibody (Bound, hereinafter abbreviated as B) and an unbound labeled antigen (Free, hereinafter abbreviated as F), thereby to determine the unknown antigen quantity in a fluid sample. First, the principle of assay by the use of this immunological analytical element (hereinafter abbreviated as analytical element or further as element) is to be described. The fluid sample in which unknown antigen is sought to be detected is brought into contact with the element in the presence of the labeled antigen. It is possible to allow the labeled antigen to co-operate with the analytical element according to one of the several methods as set forth below.

(1) a labeled antigen is added directly to a fluid sample (containing unlabeled antigen) and the fluid sample containing the labeled antigen is applied to an analytical element for assay.

(2) A labelled antigen and a fluid sample are individually added to an analytical element [e.g. (a) addition of the labeled antigen immediately before or after addition of a liquid sample and (b) addition of the labeled antigen to the element, followed by drying, and rewetting of the element when a fluid sample is added].

(3) A labeled antigen is incorporated into an analytical element so as to enable commencement of assay by mere application of a fluid sample. For example, a labeled antigen can be incorporated into a blocking layer or a detecting layer in an element or into an element constituting layer containing an immobilized antibody and capable of carrying out an antigen-antibody reaction. In any case, when a labeled antigen is to be incorporated into an element, care should be taken so that the labeled antigen may be held apart from an immobilized antibody in order to avoid too early binding of the labeled antigen to the antibody.

When a liquid sample is brought into contact with an analytical element in the presence of such a co-operating labeled antigen as described above, the labeled antigen and unlabeled antigen (unknown substance to be assayed existing in a sample) will bind competitively to the antibodies existing immobilized in the layer for carrying out the antigen-antibody reaction in the element.

As the result, when the analytical element is assayed from one side thereof, the unaltered labeled antigen quantity (F) can be measured. While the reacted labeled antigen quantity (B) (in practice, unaltered labeled antigens and other non-specific bindings exist, but they can be corrected from the value of F) can be measured, when assayed from the other side thereof.

The analytical element according to this invention can measure F and B at the same time. The quantity of the unlabeled antigen in the fluid sample can be determined with good precision by the use of the measured values of F and B.

As the first detecting layer, the blocking layer and the second detecting layer, any porous media can be employed. The "porous medium" mentioned in this invention refers to a medium, which is capable of containing a certain quantity of a fluid sample to be tested per unit area, permits the fluid sample to move freely through said medium and between medium layers and further permits the fluid sample to be contacted freely with the interfaces between medium layers. For example, there are employed membrane filters, cloths, filter papers or glass fiber filter papers. Further, as another examples of porous media, there are included those disclosed in Japanese Provisional Patent Publications Nos. 90859/1980, 101760/1982 and 101761/1982. According to the method disclosed in Japanese Provisional Patent Publication No. 90859/1980, heat-stable organic polymer particles which are unswellable with and impermeable to a fluid as described above form three-dimensional lattices together with an adhesive comprising an organic polymer different from said particles. The bound particles disclosed in Japanese Provisional Patent Publication No. 101760/1982 are formed of heat-stable organic polymer particulate units having functional groups on their surfaces unswellable with and impermeable to a fluid, which are bound through a low molecular compound. Japanese Provisional Patent Publication No. 101761/1982 discloses bound particles formed of heat-stable organic polymer particulate units having functional groups on their surfaces unswellable with and impermeable to a fluid, which are bound directly between said particulate units.

The materials disclosed in the above references can be useful as the layer comprising a porous medium according to this invention. In the present invention, the bound particles disclosed in Japanese Provisional Patent Publication No. 101761/1982 are preferably used.

As other preferable porous media, there are those disclosed in Japanese Provisional Patent Publication No. 90167/1983 and Japanese Patent Application No. 6505/1982. The former comprises functional particulate units with a core-shell multi-layer structure, having cores of organic polymeric particles having functional groups on the individual particle surfaces which are constituent material of the medium and shells of a hydrophilic polymer on said particle surfaces. The latter has a similar structure except for the core portion which is a glass or an inorganic material.

As the material constituting the aforesaid hydrophilic shell portion, there are included gelatins such as gelatin, acid-treated gelatin, etc.; water soluble cellulose derivatives such as carboxymethyl cellulose, hydroxyethyl cellulose, etc.; pullulane derivatives such as pullulane, carboxymethyl pullulane; water soluble vinyl polymers such as polyvinyl alcohol, polyvinyl pyrrolidone, polyacrylamide, etc.

It is possible to introduce functional groups crosslinkable by ionizing radiation or light onto the hydrophilic shell surface of the aforesaid particulate unit. These functional groups are described in detail in Japanese Patent Publications Nos. 5761/1981, 5762/1981 and 5763/1981.

Further, the particulate units having the above core-shell multi-layer structure can contain at least one kind of reagents at the hydrophilic shell portions of said particles. The reagent herein mentioned is a substance capable of forming a significant detecting system through co-operation with a substrate or a synthetic substrate color source and a labeled material, such as a rare earth atom ion.

Syntheses of the particulate units as mentioned above are described in detail in the above Patent Publications. They can be synthesized easily according to the procedures disclosed therein. The particulate units of this invention can carry on their surfaces an immunologically active substance such as an antigen or an antibody. The method for carrying includes the method by physical adsorption and the method in which an antigen or an antibody is carried by chemical binding.

As a physical adsorption method, an antigen or an antibody is dissolved in water or a suitable buffer, and the particulate units or the bound product of particulate units of this invention are dipped in the resultant solution to effect adsorption.

During this procedure, the buffer is a suitable buffer of 0.01 to 1M. The material to be adsorbed is used at a concentration in the range from 0.001 to 1.0%, and the particulate units or the bound product according to this invention are dipped therein to have said material adsorbed thereon.

The temperature for the above adsorption is preferably room temperature or lower and the time is preferably 10 to 100 hours.

The particulate units or the bound product of particles, after separation from the dipping solution, are preferably washed with water or a buffer to remove the antigens or antibodies which do not participate in adsorption.

As a method using chemical binding, an antigen or an antibody can be bound to the functional groups on the surfaces of the particulate units of this invention directly or through a polyfunctional reagent. As these methods, for example, the immobilization techniques of enzymes, etc. as disclosed in "Immobilized Enzyme" edited by Ichiro Chihata (published by Kodansha, 1975) can be utilized. For example, there are a diazotization method, an amidation method, an alkylation method, and methods using glutaraldehyde, hexamethylene diisocynate and the like.

As a matter of course, binding of an antigen or an antibody may be effected either by binding to the particulate units according to this invention prior to fabrication of the bound product of particles or by binding of an antigen or an antibody to the bound product of particles after its fabrication.

Further, said particulate units can also carry a protein which does not participate in the immunological reaction to be assayed for the purpose of precluding the non-specific reactions in the immunological reaction, if desired. Typical examples of these proteins are normal serum proteins of mammals, albumin, gelatin and decomposed products thereof.

As the method for carrying these proteins, there are also suitably employed the physical adsorption method and the chemical binding method similarly as described above.

The first detecting layer and the second detecting layer comprising a porous medium can be constituted by the use of the material and the method as described in detail above. In only either one of the first detecting layer and the second detecting layer, a reagent or a material participating in an immunological reaction can be incorporated, and a detecting quantity corresponding to the mode of detection of an immunological reaction under co-operation with a labeled substance can be measured.

The blocking layer according to this invention may be the same as the detecting layer as described above. It is essential, however, to incorporate a blocking agent selected from various pigments, dyes and fine metal powders for the purpose of avoiding mutual interference in measurement of the detecting quantities in the first and the second layers. The pigment or dye depend on the mode of detection employed. For example, when a reflective density at the visible or UV-ray region is employed, a white pigment or dye such as titanium dioxide or magnesium sulfate is employed. On the other hand, in case of quantifying according to a fluorescent intensity, a pigment or dye capable of absorbing fluorescence emitted from a fluorescent substance may be employed. While these are suitably chosen depending on the wavelength of the fluorescence emitted from the fluorescent substance used, there may be employed various pigments or dyes, for example, Regal ® 300 (Cabot Co.), Wachtung ® Red B pigment (E. I. Du Pont Co.). When a radioisotope is employed, it is possible to incorporate a radioactivity blocking agent such as lead.

The above pigment or dye may be incorporated into a material having previously a porosity such as cloth, filter paper or microfilter by way of staining afterwards, or by way of mixing into a spinning bath during spinning in case of a cloth. Alternatively, in case of a microfilter, a necessary amount of a dye or pigment may be incorporated in preparation thereof and the product previously colored may be used. In the bound product of particles as disclosed in Japanese Provisional Patent Publications Nos. 90859/1980, 101760/1982, 101761/1982 and 90167/1983 and Japanese Patent Application No. 6505/1982, a pigment or dye can readily be previously incorporated into the particulate units during preparation thereof, and details about such procedures are disclosed in the above publications or specification.

The blocking agent according to this invention may be contained in an amount of about 0.1 to about 25% by weight based on the weight constituting the blocking layer.

Further, the blocking layer according to this invention may also carry a non-immunogenic protein such as a serum protein of a normal vertebral animal or bovine serum albumin on its surface for the purpose of preventing non-specific binding reactions in the immunological reaction, similarly as in the detecting layer as described above.

The analytical element to be used in this invention has at least three layers of a first detecting layer, a blocking layer and a second detecting layer, which are successively laminated with the blocking layer being an intermediary layer between the first and the second detecting layers, wherein each layer is formed of a porous medium as described above and further either one of the first and the second detecting layers carries an antigen or an antibody.

For example, when using layers previously porous structures, the respective layers can be pressed with each other by the use of an aqueous solution of a hydrophilic polymer such as gelatin as an adhesive.

Further, it is also possible to effect lamination by coating. For example, the particulate units as disclosed in the above Japanese Provisional Patent Publications Nos. 90859/1980, 101760/1982, 101761/1982 and 90167/1983 and Japanese Patent Application No. 6505/1982 can be formed into the respective layers as described above by way of coating.

The aforesaid particulate units can be coated by the use of various methods. A preferable method comprises the steps of:

(1) dispersing the aforesaid particulte units in a liquid carrier which does not dissolve said particles to prepare a stable dispersion;

(2) applying the stable dispersion to a support; and (3) removing the liquid carrier while permitting said particulate units to be bound to each other at an appropriate temperature.

The "stable dispersion" herein mentioned means that the particulate units are present in the carrier without formation of an agglomerated mass. The dispersion useful for preparation of the respective layer as described above is required to be stable for a time sufficient to apply said dispersion onto a support.

For preparation of such a stable dispersion, it is possible to employ a number of methods singly or in combination. For example, as one useful method, a surfactant can be added into a liquid carrier to promote distribution and stabilization of the particulate units in a dispersion.

Typical examples of available surfactants include nonionic surfactants such as Triton ® X-100 (produced by Rohm & Haas Co., octylphenoxy polyethoxyethanol), Surfactant 10G ® (produced by Olin Co.; nonylphenoxyl polyglycidol).

The above surfactants can be used in a wide range, but generally in an amount of 10 wt. % to 0.005 wt. %, preferably 6 wt. % to 0.05 wt. %. As alternative methods, there are sonication treatment, physical mixing and physical stirring treatment, pH adjustment of said particulate units and a liquid carrier. These methods can be further useful when combined with the method as described above.

The particulate units according to this invention can be combined with each other at the contacted interfaces between mutual particulate units when removing the liquid carrier of the dispersion to prepare a porous layer. It is also useful to permit a catalyst for causing such a binding, such as an acid or an alkali, to be present in the dispersion. Particularly, it is useful to employ volatile acid catalysts (e.g. acetic acid, etc.) and others. It is also desirable to carry out the operation to remove a liquid carrier at a temperature not higher than the heat-stable temperature of the particulate units and not higher than the temperature which deactivates the substance capable of binding specifically with an immunologically active substance, preferably at a temperature of 10° to 60° C.

As the liquid carrier for the aforesaid dispersion, there may be employed an aqueous liquid. However, other liquid carriers such as various organic liquids may also be available, provided that said particulate units are insoluble in the carrier and therefore their particulate characteristics can be maintained.

Typical liquid carriers other than water include water-miscible organic solvents, aqueous mixtures of water with water-miscible organic solvent and appropriate water-immiscible organic solvent. Water-miscible organic solvents may be exemplified by lower alcohols (i.e. alcohols having alkyl moieties of 1 to 4 carbon atoms), acetone and tetrahydrofuran. Water-immiscible organic solvents may be exemplified by lower alkyl esters, and organic halide solvents such as halogenated hydrocarbons (e.g. chloroform, methylene chloride and carbon tetrachloride).

The analytical element having the layers comprising the particulate units coated thereon can be coated according to the dip coating method, the air knife method, the curtain coating method or the extrusion coating method by the use of a hopper as disclosed in U.S. Pat. No. 2,681,294, and, if desired, two or more layers can be coated simultaneously according to the method as disclosed in U.S. Pat. No. 2,761,791 and U.K. Patent No. 837,095.

As the support to be used in the element according to this invention, any liquid impervious material may be employed. However, when the final measurement of detecting quantity in immunoassay is to be conducted by a spectroscopic measurement such as a density in visible or UV-ray region or measurement of luminescence intensity as in fluorometric measurement and luminous reactions, the support is required to be light-transmissive. In this case, the support may be light-intransmissive relative to the wavelengths other than the wavelength region necessary for measurment of the detecting quantity.

In case of detection of radioactivity measurement by the use of a radioisotope, the support may be either light-transmissive or not.

Examples of the support include synthetic polymers such as cellulose triacetate, polyethyleneterephthalate, polycarbonate, polyvinyl chloride, polystyrene, etc., or glasses, metals and others.

FIG. 1 shows a sectional view of a embodiment of the element. Numeral 1 is a first detecting layer, comprising a porous medium of a bound product of particles, of which particulate units are attached with a specific reactive substance in the immunological reaction. Numeral 2 is a blocking layer of a bound product of particles, of which particulate units incorporate a blocking agent therein. Numeral and 3 is a second detecting layer constituted similarly of a bound product of particles. Numeral 4 is a support. Numeral 5 is a direction of measurement for detection.

Each of the aforesaid three kinds of layers may be a mono-layer or a plurality of layers. When each layer or laminated layers have rigidity enough to sustain the form of its own (self-supporting characteristic), the support 4 is not necessarily required.

The aforesaid three kinds of layers may be formed previously into thin films individually, and a plural number of such thin films may be pressed to an optimum thickness depending on the measuring conditions to constitute each layer before provided for use as an analytical element.

The immunoassay for which the immunological analytical element according to this invention is applicable is not limited in its detecting mode, but any immunoassay can be employed. Typical examples are radioimmunoassay (RIA), enzyme immunoassay (EIA) and fluoroimmunoassay (FIA).

For example, in RIA there are used labeled antigens such as $^{125}I$, $^{131}I$, $^{3}H$ and $^{141}C$, and in EIA there are used labeled antigens such as alkali phosphatase, glucoamylase, galactosidase, peroxidase and glucose oxidsase. Further, there are used fluorescein derivatives, rhodamine derivatives and rare earth chelates compounds in FIA. Particularly, RIA and FIA are preferably used for the analytical element.

The detection mode of the reaction includes various methods such as the competitive method, the sandwitch method, the two antibody method, etc. The various detecting assays and various reaction detecting modes may be used in combination as desired. These are described in detail in textbooks and reviews, as in "Radioimmunoassay" edited by Minoru Irie (published by Kodansha, 1974) or "Enzyme Immunoassay" edited by Eiji Ishikawa, Tadashi Kawai & Kiyoshi Miyai (published by Igaku Shoin, 1978).

The immunoassay by the use of the immunologicl analytical element according to this invention improves the precision of immunoassay by measuring both of Bound and Free. This invention is illustrated by referring to the following Examples.

EXAMPLE 1

A suspension of 10 parts by weight of a poly(styrene-co-n-butyl methacrylate-co-glycidyl methacrylate) (75:15:10 wt. %) with a average particle size of 21 μm suspended in a phosphate buffer (0.01M, pH 7.0) containing 0.5 parts by weight of a nonionic surfactant Triton ® X-100 (produced by Rohm & Haas Co.) and 0.1 part by weight of bovine serum albumin (produced by Wako Junyaku Co.) was coated on a polyethyleneterephthalate support (film thickness: 180 μm) while controlling the coated amount to 1.6 g/dm² with respect to said particles, followed by drying at 42° C. for 30 minutes by using a film drier, to prepare a first detecting layer.

On this detecting layer were formed similarly a blocking layer and a second detecting layer to prepare an analytical element for assay of human α-fetoprotein.

The blocking layer and the second detecting layer are as follows.
Blocking layer:

Black particles of poly(styrene-co-n-butyl methacrylate-co-glycidyl methacrylate) (75:15:10 wt. %) with an average particle size of 21 μm containing only 2 wt. % of Regal 300 ® (produced by Cabot Co.). Coated amount: 0.8 g/dm².

Second detecting layer:

The same particles as employed for the first detecting layer, on which rabbit anti-human α-fetoprotein antibodies (produced by Dacopak Co., Denmark) are adsorbed. Coated amount: 1.6 g/dm².

Test sera were prepared by adding to a serum, prepared by removing α-fetoprotein from a normal human serum with an immunological adsorbent, $1 \times 10^{-7}$M FITC (fluorescein isothiocyanate) labeled α-fetoprotein as the labeled antigen and various concentrations of 0 to $1 \times 10^{-6}$M of α-fetoproteins as unlabeled antigens. Each 10 μl of serum was applied to the analytical element, followed by incubation at 37° C. for 20 minutes.

Then, the fluorescent intensities of fluorescein were measured from the first detecting layer side and the second detecting layer side by means of a reflective fluorometer having an excitation filter at 485 nm and an emission filter at 525 nm, to obtain the results shown in Table 1.

TABLE 1

| Conc. of α-feto-protein in test serum (M) | Intensity of fluorescence: 1st detecting layer side | Intensity of fluorescence: 2nd detecting layer side | Total |
| --- | --- | --- | --- |
| 0 | 28 | 509 | 537 |
| $5 \times 10^{-8}$ | 102 | 418 | 520 |
| $1 \times 10^{-7}$ | 141 | 373 | 514 |
| $5 \times 10^{-7}$ | 208 | 318 | 526 |
| $1 \times 10^{-6}$ | 232 | 279 | 511 |
| $2 \times 10^{-6}$ | 250 | 283 | 533 |
| Phosphate buffer (Control) | 22 | 27 | 49 |

As apparently seen from the Table, α-fetoproteins at respective concentrations can be discriminated only by measurement of the first detecting layer or the second detecting layer, but the total values of the first detecting layer side and the second detecting layer side do not coincide with each other.

This is probably due to various factors such as fluctuations of the light source during fluorescence measurement, etc., and therefore measurements from only one side involve the risk of such errors, and there is no means to know the extent of such errors. Reliability of the measured values can be confirmed for the first time by measurements from both sides as practiced by this invention.

EXAMPLE 2

To the analytical element of Example 1 were added dropwise each 10 μl of $1 \times 10^{-7}$ M FITC-α-fetoprotein as the labeled antigen and $1 \times 10^{-7}$M test serum as unlabeled antigen, followed by incubation at 37° C. for 20 minutes, and the fluorescent intensities were measured similarly as in Example 1 to obtain the results shown in Table 2.

TABLE 2

| Test No. | Intensity of fluorescence: 1st detecting layer side F | Intensity of fluorescence: 2nd detecting layer side B | Total (F + B) |
| --- | --- | --- | --- |
| 1 | 100 | 302 | 402 |
| 2 | 96 | 263 | 359 |
| 3 | 86 | 261 | 347 |
| 4 | 102 | 323 | 425 |
| 5 | 98 | 301 | 399 |
| Fluctuation coefficient (%) | 6.46 | 9.32 | 8.38 |

To calculate here the values of F/(B+F) and B/(B+F) for respective test results (correction corresponding to fluctuations), the following values can be obtained:

For F/(B+F) coefficient of variation: 4.14%
For B/(B+F) coefficient of variation: 1.38%

Thus, by conducting measurements from both sides of the first detecting layer and the second detecting layer according to this invention and applying the correction as calculated above, reproducibility can clearly be enhanced.

We claim:

1. An immunoassay method for measuring an immunological antigen in a fluid sample, which comprises:
    contacting said fluid sample with a first detecting layer of an immunological analytical element in the presence of a labeled antigen, said element comprising sequentially the first detecting layer, a blocking layer, a second detecting layer and a substrate and at least one of said first and second detecting layers contains an antibody capable of binding specifically to said antigen and labeled antigen to carry out a competitive reaction of said antigen and said labeled antigen with said antibody; and
    separately measuring the amount of the unreacted labeled antigen and the amount of binding complex of said labeled antigen and said antibody of both said first and said second detecting layers to determine the amount of said antigen in said fluid sample.

2. The immunoassay of claim 1, wherein said first and second detecting layers comprise a porous medium.

3. The immunoassay of claim 2, wherein said blocking layer comprises a porous medium.

4. The immunoassay of claim 3, wherein at least one of said layers comprise a porous medium selected from the group consisting of cloths, filter papers, glass filter papers and microfilters.

5. The immunoassay of claim 3, wherein at least one of said layers comprise bound particles formed of heat-stable organic polymer particulate units having a functional group on the surface thereof, said particulate units being unswellable with and impermeable to said fluid sample and said bound particles being bound directly between said particulate units.

6. The immunoassay of claim 1, wherein at least one of said layers are formed by coating high-molecular polymer particulate units with the use of particles of an organic synthetic polymer.

7. The immunoassay of claim 6, wherein said high-molecular polymer particulate unit is a core-shell multilayer structure having hydrophilic shells around cores unswellable with and impermeable to said fluid sample.

8. The immunoassay of claim 1, wherein said first detecting layer, blocking layer and second detecting layer comprise a same porous medium.

9. The immunoassay method of claim 1, wherein said labeled antigen is added directly to a fluid sample containing unlabeled antigen and the fluid sample containing the labeled antigen is applied to an analytical element for assay.

10. The immunoassay method of claim 1, wherein said labeled antigen and a fluid sample are individually added to an analytical element by the addition of the labeled antigen immediately before or after addition of said fluid sample.

11. The immunoassay method of claim 1, wherein said labeled antigen and a fluid sample are individually added to an analytical element by the addition of the labeled antigen to the element, followed by drying, and rewetting of the element when a fluid sample is added.

12. The immunoassay method of claim 1, wherein said labeled antigen is incorporated into an analytical element so as to enable commencement to assay solely by contacting a fluid sample.

13. The immunoassay method of claim 1, wherein said antibody is contained in said first detecting layer.

14. The immunoassay method of claim 1, wherein said labeled antigen is slected from a radioactive labeled antigen, an enzyme labeled antigen and a fluorescent labeled antigen.

15. The immunoassay method of claim 9, wherein said antibody is contained only in said first detecting layer.

16. The immunoassay method of claim 10, wherein said antibody is contained only in said first detecting layer.

17. The immunoassay method of claim 11, wherein said antibody is contained only in said first detecting layer.

18. The immunoassay method of claim 12, wherein said antibody is contained only in said first detecting layer.

* * * * *